(12) United States Patent
Ramarethinam

(10) Patent No.: US 6,855,351 B2
(45) Date of Patent: Feb. 15, 2005

(54) PESTICIDE FORMULATION CONTAINING AZADIRACHTIN (NOT LESS THAN 300 PPM) AND SALANIN IN A FORMULATED PRODUCT WITH NEEM OIL

(75) Inventor: Santhanam Ramarethinam, Coimbatore (IN)

(73) Assignee: T. Stanes and Company Limited, Tamil Nadu (IN)

( * ) Notice: Subject to any disclaimer, the term of this patent is extended or adjusted under 35 U.S.C. 154(b) by 137 days.

(21) Appl. No.: 10/118,867

(22) Filed: Apr. 9, 2002

(65) Prior Publication Data

US 2003/0170330 A1 Sep. 11, 2003

(30) Foreign Application Priority Data

Mar. 5, 2002 (IN) .................................... 116/MAS/2002

(51) Int. Cl.[7] ........................ A61N 65/00; A61K 35/78; A01N 25/00
(52) U.S. Cl. ........................................ 424/761; 424/405
(58) Field of Search ................................ 424/761, 405

(56) References Cited

PUBLICATIONS

J. Leatemia et al.; "Crude Seed of Annona Squamosa (Annonaceae) as a Potential Botanical Insectide" ESA 2001 Annual Meeting Dec. 10, 2001.
D. Cortes et al.; "Bis–tetrahydrofuranAcetogenins from Annonaceae" Phytochemistry, 32(6) Mar. 25, 2002; 1993; pp. 1467–1473—Internet abstract.
D. Hopp etal.; Squamotacin: An annonaceous Acetogenin with ctotoxic selectivity for the human prostate cell line (PC–3) Journal of Natural Products, 59(2) 1996; pp. 97–99 Internet abstract.
X.Li et al., Bullatacin, Bullatacinone, Squoamone, a New Bioactive Acetogenin, from the Bark of Annona Squamosa, Journal of Natural Products, 53(1) 1990 pp. 81–86—internet abstract.
M. Londershausen, et al.; "Molecular Mode of Action of Annonins" Pesticide Science, 33(4) pp. 427–438 1991; internet abstract.
M.Londershausen, etal.; "Annonins– Mode of Action of Actogenins Isolated from *Annona squamosa*" Pesticide Science, 33(4) pp. 443–445 1991—internet abstract.
A. Saluja et al.; "Phytochemical Study of Annona Squamosa" Fitoterapia, 61(4) 1989; pp. 359–360—internet abstract.
J. Leatemia et al.; "Bioactivity of Crude Extracts of Annona spp. (Annonaceae) Against Lepidopteran Larvae"; AGM Agenda 2000—internet abstract.
Annona squamosa, Pacific Island Ecosystems at Risk (PIER); 2000—internet abstract.
V. Mariappan et al.; Custard Apple Oil, Neem Oil, and Their Mixtures: Effect on Survival of Nephotettix Virescens and on Rice Tungro Virus Transmission Proc. $2^{nd}$ Int. Neem Conf. 1983, pp. 413–429.
Australian New Crops, Listing of Useful Plants of the World, 1997; internet site Mar. 23, 2002.
G. Raman, et al.; "Field Evaluations of Botanical Agents from *Annona squamosa* Against Castor Semilooper, *Achoea janata*"; Proc.Nat. Symp.Biol.Cont.Agri.Forest,Medi Vet.Sci. 1999.
"Fruits from America, An Ethnobotanical Inventory" Annona squamosa; 1972,1993,1997; internet site.
Annual Report 2000 "Output 5. Information on Bio–efficacy of Natural Enemies, Bio–pesticides, and Agronomic Practices for Integrated Management of Pod and Stem Borers"—internet site.
Cherimoya Annona cherimola—internet site printed Mar. 25, 2002.

*Primary Examiner*—Chris Tate
*Assistant Examiner*—Randall Winston
(74) *Attorney, Agent, or Firm*—Norris & McLaughlin & Marcus

(57) ABSTRACT

The present invention relates to the extraction of azadirachtin from the Neem seed kernel, wherein a storage stable Neem oil-based emulsion is prepared in concentrate form for pesticide use. The emulsion comprises neem tetranortriterpenoids and neem limonoids including Azadirachtin not less than 300 ppm. The invention also relates to controlling pests by combining extracts of Neem and the custard apple, wherein the custard apple does not affect the pesticidal properties of the limonoids.

24 Claims, No Drawings

PESTICIDE FORMULATION CONTAINING AZADIRACHTIN (NOT LESS THAN 300 PPM) AND SALANIN IN A FORMULATED PRODUCT WITH NEEM OIL

OBJECT OF THE INVENTION

The object of the invention is to aim at extraction of azadirachtin from neem seed kernel, in a very simplified but efficient manner which has highest level of azadirachtin and without allowing mycotoxins contamination, and consequently to prepare neem oil based emulsion concentrate, a stable pesticide containing mostly the limonoids of neem as it occurs in nature in the neem seed, and hence fit to be called as neem based pesticide.

In addition, the invention also aims at extracting the constituents of custard apple from immature fruits and leaves as well as from mature seeds using the desired solvents and dousing it into a neem seed kernel extract in the course of the preparation of neem oil emulsion concentrate without affecting the pesticidal properties of the limanoids of neem leading to a botanical pesticide, a combination of neem and custard apple whereby the pesticidal potency of neem as well as of custard apple are exploited for the benefit of controlling pests which posses mere susceptibility to either neem or custard apple and hence more order of pests can be controlled through combination.

The first object of the invention is to form storage stable neem oil emulsion which contains a desired amount Azadirachtin to be an effective pesticide and also combine these with the extracts of custard apple to exploit the pesticidal properties of custard apple in the immature fruit stage, seed stage as well as in the leaves and thereby producing a totally natural and effective herbal pesticide containing the characteristics of neem and custard apple leading a preparation of neutral pesticide which benefit more number of target pests in the process of pest control.

It is another object of the invention to extract neem oil as well as Azadirachtin simultaneously from the neem seeds.

The other object of the invention includes, to extract out the constituents of custard apple from its immature fruits, immature seeds and leaves and dousing it in the neem oil preparation to enhance or improve the pesticidal properties of neem in combination with the synergistic constituents of custard apple extracts.

It is another object of the invention to form environmentally safe pesticide taking advantage of the pesticide characteristics found in plants like neem tree and custard apple in their specific parts like neem seeds as well as in the immature fruits, mature seeds and leaves of Annona Squmosa and Annona Reticulata—commonly referred to as Custard Apple and developing a herbal based combination pesticide, which in no way inhibits the main objective of inventing an environmentally safe pesticide a combination pesticide.

It is another object of the invention to form an pesticide which contains neem oil, desired amount of Azadirachtin emulsifying agent and desired preparation of extracts from immature fruits of Annona Squmosa and Annona Reticulata.

As per the invention, neem oil as well as Azadirachtin are simultaneously extracted from the neem seeds and the extracts of custard apple Annona Squmosa and Annona Reticulata from their immature fruits, seeds and leaves, extracted separately and doused in the preparation at appropriate time as described in the process of the preparation of neem oil emulsion based pesticides.

The invention has been described and illustrated with preferences and ranges in the foregoing paras, much variation therein may be done by those skilled in the art without departing from the sport and scope of the invention claims.

Further to produce it in a most economical and inexpensive methods, with minimal chemicalisation and to produce through simple techniques which are more natural than chemical and at the same time extract the limonoids of neem seed with high yields of potent tetranortripenoids including azadirachtin (an antifeedaant limonoid) with high oil content as high as 85.00% and further the potency of such pesticide so produced is also enhanced to a great extent without affecting the basic concept of safe and environment freely pesticide through the deployment of the extracts of custard apple obtained from the immature fruits and seeds and leaves of Annona Squmosa and Annona Reticulata production of a combination pesticide of herbal base which is safe, environment friendly pesticide and further that which enhanced the pesticide potential of the resultant pesticide and results in greater bioefficacy by increasing the control capability of more number of target pests.

DESCRIPTION

The invention herein described relates to a process for preparing a neem based emulsifying concentrate containing azadirachtin not less than 300 ppm, neem oil more than 85%, aportic solvent by volume 3.90% and less than 5.0% and not more than 8.00% percent of ethoxylated vegetable oil containing long chain fatty alcohol series from C8 to C18 by volume and which can enter into a stable oil water emulsion without degrading azadirachtin content along with addition of not more than 5% of the extracts from custard apple immature fruits, seeds and leaves without degrading the efficacy of Azadirachtin contained under the same time having Azadirachtin synergisticism with neem limonoids facilitating the enhancement of pesticidal potency and thereby leading to Azadirachtin combination pesticide with high bio-efficacy standards without affecting the safe and environment friendly nature of neem based combination pesticides. This formulation formulated by the process of this invention has found its application and usage as a pest control formulation in Agriculture, and in Veterinary with higher bioefficacy and potency to control more number of target pests.

There are a number of chemical, broad-spectrum pesticide formulations, systemic and contact, available for the control of insect pests that attack and damage food crops and economically important crops. These chemical pesticides aim at pest eradication and kill the pests and insects and in this process all the insects good and bad insects are killed and in addition they not only affect the ecosystem but also pollute the atmosphere with chemical, kills the natural enemies to pests and other beneficial microorganisms and pollute the water we drink, air we breathe and food we eat. The pests or the insects also develop resistance to the pesticide in the coarse of time on continuous usage. Hence, a need for pest control agent which are biodegradable that which are ecofriendly, biodegradable, that does not affect the beneficial organisms, non-toxic to ecosystem and human beings and at the same time effective against the target pest or insect is felt and the answer is this invention at least partly if not fully.

The Pesticidal plant that has drawn the attention of many scientists, researchers, and industrialist all over the world the Neem (*Azadirachta indica A. Juss*) is widely spread in India and Pakistan and some parts of South East Asia. The neem tree and its various parts (Leaves, Seeds, Bark etc.,) have found its application in various fields like food, medicine, and cosmetics and in agriculture. Out of the various parts of the neem tree the neem seeds in different forms like neem oil, neem cake, neem seed extracts have found wide application in various fields. In agriculture the Neem seeds and its various forms are used as nitrogen fertilizer, pesticide, fungicides, nematicides etc., the usage of neem seed is more advisable than usage of other parts like green leaves, bark and not because these will affect the life if the neem tree where as neem seed will not.

Similarly, the additive from the satellite plant used in this preparation is a natural combination pesticide viz., Annona Squmosa and Annona Reticulata only referred to as custard apple also known as plants with pesticidal properties. Many scientific references indicate that the various parts of this plant have pesticidal property. The extracts of its different parts viz., immature fruits, seeds and leaves have been scientifically found to have insecticidal property. The aqueous extracts of different parts of custard apple were tried in a crude form in the control of a number of pests that commonly affects different agricultural crops. It is well known that custard apple is used as a common fruits in tropical countries including mid and southern parts of India. There are a number of references and literature available to prove that it has pesticidal property (G. V. Raman et al 1999; Carmen Zafra-polo et al 1998; Srinivasa Rao et al 1996; J. A. Leatemia and Mury B. Isman university of British Columbia Vancouver, BC, Canada).

There are a number of references and literatures available. (Schmutterer et. Al 1980; Schmutterer and Ascher, 1984, 1987; Jacobson 1986, 1988; Randhawa and Parmar 1993) Neem seed is a storehouse of over 100 tetrenortriterpenoids and diverse isoprenoids (Devakumar and Sukh Dev 1993) with insecticidal property.

The most important and biologically proven active constituent of neem seeds is the Azadirachtin. Several isomers of azadirachtin have been identified and out of the isomers the most potent and active component is the Azadirachtin A.

There are a number of articles reporting the insect antifeedant and insect growth inhibitory properties of azadirachtin for a variety of insect pests (Butterworth J. H. and Morgan, E. D., J. Chem. Soc. Chem. Cummuns, 23 1968; Leushner, K., Naturwissenschaften, 59,217,1972; Ruscoe, C. N. E. Nature, lond., 236,466,1972 Schmutterer, H and Rembold, H. Z, Angew. Ent. 2,179–188, 1980; Warthen, J. D. Jr., ARMNE-4 USDA, SEA, Agricultural review and manuals, 1979; Kubo, I and klocke, J. A., Agricultural and Biological Chemistry, 46,1951, 1982; Champagne, D. E., Koul, O., Isman, M. B., Scudder, G. E. and Towers, G. H. N., phytochemistry, 31, 377,1992).

There are a number of articles contributing insecticidal property to the extracts from seeds, immature fruits leaves of Annona Squmosa and Annona Reticulata. The constituents of custard apple extracts from immature fruits, mature seeds and leaves are safe and have no mammalian toxicity. Toxicity to fish is known.

Azadirachtin has also been reported to be Non-mutagenic (Jacobson, M., proceedings of the first International Neem conference, Rottach Egern, 33, 1980; in natural pesticides from the neem tree, *Azadirachta indica A. Juss*, Schmutterer, H., Ascher, K. R. S., German agency for technical cooperation, Eshborn, German, 1981) and it appears to have no apparent mammalian toxicity (Nakashini, K., Recent advances in phytochemistry,5,283, 1975; Morgan, E. D., Proceedings of the First international neem conference, Rottach Egern, 43, 1980; in Natural pesticides from neem tree, *Azadirachta indica A. Juss*, Schmutterer, H., Ascher, K. R. S., Rembold, H., Eds., German Agency for Technical cooperation, Eschborn, Germany 1981).

It has also been reported that neem products with or without azadirachtin has shown very good control over 300 inset pests and infections by nematodes viruses and some pathogenic fungi (Devakumar. C, and Parmar. B. S., 1993). The other limonoids or the bitter principle such as Azadirachtin, Salanin, Meliantriol, deacetylsalanin and nimbin contained in the neem oil are also responsible for the pesticidal activity of neem oil (Vimal O. P and Naphade, K. T., 1980 Jour. Scic. Ind. Res. Vol. 39, P 197–211)

Though individually neem and custard apple have been reported to have varied insecticidal properties so far no attempts have been made to understand the efficacy of the combination, viz., neem oil with custard apple extracts in the production of a safe and eco friendly pesticide towards the control of agricultural pests.

Plant based pesticides are normally preferred due to its shorter persistence in the atmosphere, biodegradable, non-toxicity to the ecosystem, atmosphere, human beings, and beneficial microorganism, harmless to birds, fish, and low toxicity to flora and fauna. Neem oil, extracted from neem seeds of the neem tree, is known for its high pesticidal value. Due to its low coverage, low evaporation capacity from the leaves, and as it sticks to the surface of the leaves it stays in the leaves for a long time and turns toxic to the plants, hence neem oil spray per say is neither efficient nor preferable to neem oil based E.C. formulation with Annona sps. Additives.

The pesticides produced with combination of neem and custard apple extracts as referred above has been found to be non-toxic, eco-friendly and efficient as pest control agent with increased bio-efficacy with synergicism with neem and without any hazardous effects to mammals and non polluting the atmosphere.

Hence from the above studies, it is obvious that azadirachtin is considered to be a promising environmentally compatible, non-toxic insect pest control molecule for plant protection. This molecule in its pure form has not come to commercial use because it is expensive to isolate it in a pure form from the neem seed/kernel extract and it is a very complex molecule for an economical chemical synthesis. Azadirachtin has also been found to degrade rapidly due to environmental factors such as UV radiation in sunlight, heat, air moisture, acidity and enzymes present in foliar surfaces (Sundaram, K. M. S. and Curry, J., Journal of Pesticide Science, 41, 129, 1994).

These negatives of the Azadirachtin which may express itself under unfavourable agro-climatic condition, is neturalized by this formulation. The Bio-efficacy aspects is further enhanced through the addition of the extracts of custard apple obtained from immature fruits, mature seeds and leaves of the Annona Squmosa and Annona Reticulata plants which extract has synergism with other limonoids of neem and does not in any way neither fundamentally alter the toxicological properties of the neem preparation not its eco-friendly nature.

A scan through the literature indicates no such prior art. There are so much idea as expressed to produce a combination pesticide with neem and custard apple seem to have occurred in the past even through individual plants like custard apple ones we studied extensively for its pesticidal properties.

In the prior art, Butter worth and Morgan (Butter worth, J. H. and Morgan, E. D., J. Insect Physiol., 17, 969, 1971)

prepared azadirachtin from neem seeds by extraction with ethanol, partitioning of the concentrate of ethanol extract between methanol and light petroleum, chromatography of partition product, from methanol phase leading to azadirachtin containing fractions, partitioning again by preparative layer chromatography of azadirachtin containing fractions resulting in azadirachtin (1.5 g.). The product obtained in this process (76 g.) would be economical to obtain but it would be viscous and oily due to the presence of water soluble compounds and therefore, it is not suitable for preparing good formulations, and the steps involved in the process are too many and makes it cumbersome and not simple for commercial application in large scale and therefore requires further simplification in processing by less expensive less cumbersome techniques for the preparation of a ready to use product enriched in azadirachtin. (Moreover the solvent used is only ethanol and it has been reported by many that 100% extraction of the azadirachtin from the neem seed is not possible and a combination of solvents is always recommended for better extraction of azadirachtin from the neem seeds.)

In the prior art, Uebel, Warthen, Jr. and Jacobson (Uebel, E. C., Warthen, Jr. J. D. and Jacobson, M, J. Liq. Chromatogr., 2, 878, 1979) have isolated azadirachtin from neem seeds/kernels (48.2 kg.) involving grinding neem seeds/kernels in hexane in a Waring blender, filtration of the homogenate to give a residue marc, soxhlet extraction of powdered marc so obtained with acetone for 24 h, washing of acetone extract with hexane, water, and hexane, and treatment of washed acetone extract with 70/30, 75/25, methanol/water, treatment of 70/30, 75/25 methanol/water soluble parts with 75/25, diethyl ether/acetone to give 75/25, diethyl ether/acetone soluble azadirachtin containing fractions, chromatography (Phase-bonded C-18, Hi-florisil) of diethyl ether/acetone fractions leading to azadirachtin (8.7 g. 90% purity). The product obtained after treatment of acetone extract with 70/30, 75/25, methanol/water in the process by this process requires modification, avoiding diethyl ether a highly inflammable solvent and difficult for solvent recovery and repetitive use in large scale operations. Furthermore, the process detail require greater simplification in steps for large scale operations such as, pre-extraction of neem seed kernels with hexane, before extraction with acetone, should also be avoided since azadirachtin is unstable at the boiling point of acetone (57.degree. C.) compared to ambient temperature. Acetone is a low boiling solvent and it is also not an excellent solvent for recovery and repetitive use in large-scale operations economically. This method is therefore, not well suited for producing emulsified neem oil enriched azadirachtin, because the operations are too many, hazardous uneconomical and inconvenient for large-scale preparations.

In the prior art, Feuerhake (Feuerhake, K. J., Proceedings of Second International Neem Conference, Rauischholozhausen, 103, 1983; in Natural Pesticides from the neem tree and other Tropical plants, Schumutterer, H. and Ascher, K. R. S., Eds., German Agency for Technical Cooperation, Eschborn, Germany, 1984), investigated the suitability of the technical solvents (a), methyl tertiary butyl ether (MTB); (b), methyl isobutyl ketone (MIK); (c), methyl ethyl ketone (MEK); (d), water; (e), methanol; (f), azeotropic mixture of methanol and MTB, (AZT); (g), acetone and (h), butanol and they have recommended AZT for the preparation of azadirachtin enriched extracts and found that water is not a convenient solvent for extracting azadirachtin since its solubility in water is low. Use of neem oil and p-amino benzoic acid for protection of azadirachtin is also a prior art. There are a few examples of other commercial formulations based on neem seeds/kernels/oil are Azatin, Neemguard which is a neem oil formulation, Neemgold containing 300 ppm azadirachtin and Neemazal F but these preparation are fundamentally different from the expressed in this invention.

The procedure consists of the following steps; (1), ground neem seed kernels were first extracted in a soxhlet with petroleum ether to remove fatty matter; (2), the extraction was continued with solvents such as MIBK and MTB or acetone or MeOH or AZT or MEK or butanol for 10 h.; (3), the residue from AZT extract after removal of the solvent was treated with methanol; (4), the methanol soluble portion from step 3, was subjected to liquid-liquid extraction with methanol 50% and light petroleum giving rise to AZT-VR-NR in a yield of 1–1.5% which is expected to be enriched azadirachtin.

In the broadest scope the invention relates to a process which relates to environmentally safe and storage stable, neem oil emulsion, which emulsion contain required amount of azadirachtin.

In the present invention azadirachtin is extracted from neem seeds alongwith neem oil. In addition, the constituents of the neem cake and the neem seed kernels are extracted in as is done elsewhere in other inventions through liquid phase of the solvent by percolating into the ground bio-mass of the neem seed kernels but here, the liquid phase of the solvent is converted into a gaseous state and these vapourised state of the solvent in a gaseous condition is allowed to pass through the ground biomass where the vapours condense and reconverted to a state of liquid phase again and thereby percolates efficiently into the dough of the biomass and in the process condensation acts as a liquid solvent percolates freely and dissolves the limonoids of the neem. The percolation initially in a gaseous state and subsequently into a liquid state makes the process of extraction more effective then the liquid state solvent extraction procedure alone as hitherto employed by other in such similar processes. The lipid and lipo proteins in the neem oil protect the limonoid azadirachtin from UV degradation.

In addition, in this invention the pesticidal potency of custard apple from the immature fruits, mature seeds and leaves of Annona Squmosa and Annona Reticulata are also exploited through its addition with neem, resulting in "neem annona" combination pesticide preparation. The tender fruits of custard apple (Annona Squmosa and Annona Reticulata—either individually or in combination), mature seeds and leaves were crushed and ground to a dough and to the biomass dough the vapours of different solvents are made to condense, percolate and the infusion is collected which contains the constituents that exists in the different parts of the plants i.e., Annona Squmosa and Annona Reticulata and these constituents are known are proven to have pesticidal properties.

In the present invention a process for preparing a neem based emulsion concentrate containing azadirachtin not less than 300 ppm, neem oil as much as 85%, aportic solvent by volume 3.90% and less than 5.0% and not more than 8.00% percent of ethoxylated vegetable oil containing long chain fatty alcohol series from C8 to C18 by volume and which can enter into a stable oil water emulsion without degrading azadirachtin content, alongwith the extracts of custard apple from the immature fruits, mature seeds and leaves of Annona Squmosa and Annona Reticulata extracted using different solvents and doused in this preparation at the stage of addition of ethoxylated vegetable on and that too to a level not exceeding 5% by volume, which does not affect fundamentally the basic qualities of Azadirachtin and at the some time synergistic in action with other neem limonoids leading to a preparation of a combination pesticide containing neem oil and neem extracts along with Azadirachtin and also the constituents of custard apple (Annona Squmosa and Annona Reticulata) and which involves the following steps:

I. Preparing the Seeds
   a. Collection of Neem Fruits: Collection of Neem fruit at appropriate time of maturity from designated field grown in favorable agro-climatic conditions so as to have optimal limonoids content in general and Azadirachtin in particular to have the desired pesticidal properties.
   b. Extraction of Neem Seeds: Fruits are subjected to pulping, washing with polar solvent including water and seeds are extracted. The seeds so extracted are dried in a clean floor and covered with plain transparent polythene sheets in batches, either in sun wherein the seeds are exposed to the sun rays through polythene sheets which is spread over the said seeds to prevent contamination and/or drying the said seeds in controlled temperature between 70° C. and 80° C. in column dryers/batch driers.
   c. Anti Fungal coating of seeds: The extracted seeds are coated with Anti-fungal preparation like *Trichoderma viride* or *Trichoderma hamatum* or *Trichoderma harzianum* or Chemicals like Bronopol (Dinitro Dibromo propane 2,3 diol) in a mechanized slurry seed treated and the so treated seeds are packed in jute gunny bags and are stored in well ventilated godowns which are designed to suit seed storage.

II. Separating Neem Oil and Neem Cake from Neem Seeds
   a. Crushing of seeds: Crushing the said seeds in carried out in wooden crushers, and driven with bullock (power driven motors). The power driven wooden crushers (rotary crushers) are used to crush the said seeds at times of need but care is taken to avoid rise in temperature.
   b. Extraction of oil: Extraction is through the addition of Palm Sugar or solvents or molasses, which essentially facilitates separation of oil under low temperature from the crushed biomass of the neem seed kernels. The separated neem oil is stored in is well designed storage vessels and the leftover residue biomass is called neem cake is also packed in fresh jute bags and stored carefully. The neem oil obtained may contains Aflatoxin, alongwith fatty acids and terpenoids. Hence the oil is tested and Aflatoxin if present within limits is neutralized or the oil is rejected.

III. Preparing Neem Oil
   a. Neutralisation of neem oil: The said neem oil is then subjected to chemical neutralization for the removal of Aflatoxin.
   b. Precipitation of fatty acids: The said neem oil containing fatty acids (saturated and unsaturated) alongwith other terpenoids is subjected to precipitation. The free fatty acids are made to precipitate in lye solution. The amount of lye solution added to the said neem oil for precipitating the said free fatty acid is calculated by determining the percentage of said free fatty acid in the oil. This process is done to make the said neem oil less dense lighter and to separate the said fatty acids without subjecting it to with any chemical process or using any organic solvents like hexane, petroleum ether or benzene. The said precipitation process is repeated over a number of times until all fatty acids is separated from the neem oil.
   c. Separation by filtration: Subjecting the said resulting mix comprising of said neutral neem oil and said precipitated fatty acid to filtration process by means of a filter cloth i.e. passing the said oil through the filter cloth. In this process the precipitated fatty acids, which are the solid portion of the mix, are removed from the liquid portion of the said mix to get a semi-pure neutral neem oil with lower density.
   d. Separation by centrifugation: The semi-pure neutral neem oil with reduced density is then subjected to centrifugation to separate the remaining fatty acids and to obtain desired neutral less dense neem neem oil.
   e. Addition of preservatives: Such as Sodium Benzoate singly or in association with such other preservatives to the neem oil to maintain it at the same level of desired qualities during storage.

IV. Preparing Azadirachtin Concentrate Extract
   a. The said neem cake separated through crushing of the said seeds is crushed to a particle size fit enough for making soft dough, giving minimal time for soaking i.e particle size being 60 mesh.
   b. The said neem cake is then further ground from particle size of 60 mesh into powder. This ground powder is termed as Neem cake powder.
   c. This neem cake powder is soaked in water at the rate of 10 kgs in 20 litres of water for 12 hrs to yield soaked neem caked powder B.
   d. The said Neem seeds are decorticated and the kernels is separated.
   e. The said kernel is then soaked in water with electrical conductivity normally not greater than 0.05 m mhos $cm^{-2}$ and such that 10 kgs are soaked in 20 litres of water and kept overnight or till the kernel becomes soft, which is normally 12 to 14 hours approximately.
   f. The said soft kernel is ground in a grinder using one or more polar solvent to yield a neem kernel dough C.
   g. Neem kernel dough C and soaked neem cake powder B are mixed in equal proportion and blended to form a dough D. This blend of 1:1 of neem seed kernel dough C and neem cake powder B forming the dough D is taken into hot vapour perculator system having porous bottom and air tight lid.
   h. To separate the residual oil and azadirachtin, one or more polar solvent vapour is passed through the dough D which condenses and percolates and extracts the soluble terpenoids E. The purity of vapour of polar solvent that penetrates is almost 100%. For every 10 kilos of dough mix D, 30 litres of 99% polar solvent is used for vapour condensation.
   i. To remove the excess solvent from the extract the technique of vaccum vapourization process is employed with a common known system of vapourization at a temperature, which is adjusted to suit the point of vaporization of individual polar solvent. If for example polar solvent used is ethanol it is normally 40° C. to 60° C., temperature is adjusted to recover the solvent ethanol. The resultant residue is a semi-pure terpenoids extract (F) of neem.
   j. Concentrating the semi-pure terpenoids extract F with condensation and by means of cold vaccum evaporator process so as to yield extract G.
   k. Mixing the extract G with non-polar solvents at the temperature range between 30–70 degrees such as to separate the liquid phase containing the azadirachtin and other terpenoids from the organic phase. The liquid phase and the organic phase together form the final slurry H.

l. After the solvent extraction, the residue dough mixture is further subjected to filtration for separating solid and liquid. The filtration may be carried out following two methodologies:

m. In the first method the residue dough mixture is subjected to centrifugation with an industrial centrifuge at 6000 rpm for an hour or more and the solid and liquid phase are separated.

n. In the second method the residue dough mixture is packed in filter bags and subjected to pressure in a hydraulic press and the liquid portion is separated from the solids under high pressure. Normally pressure employed in the hydraulic press is 100–110 psi.

o. The said liquid phase obtained in either case i.e., (i) centrifugation at 6000 rpm or (ii) In hydraulic press will yield a new terpenoids concentrate. This slurry further processed through different solvent extraction herein above described in preceding paras to yield the thick liquid portion I.

p. The H, either individually or a mixture thereof so obtained will be processed in different batches and the resultant mixture are mixed to yield a thick slurry J.

q. Said final portion J containing the terpenoids including azadirachtin and salanin as the major constituents in association with other synergistic compounds is further concentrated by passing the resultant thick liquid through a membrane filter following the process of Reverse osmosis filtration through membrane filters. In this process the solutions is subjected to filtration of different compounds with different containing different molecular weight. So the compounds are separated on the basis of their molecular weight. The separation is so done that compounds having molecular weight>1000 are separated from the compounds having molecular weights<1000. The solvent containing all the compounds having molecular weights<1000 is collected to yield slurry K. The molecular weight of azadirachtin is 720. Therefore the solvent portion containing all the compounds having molecular weight<1000 will contain Azadirachtin also.

r. Purifying the said thick solution K containing the lower molecular weight compounds including azadirachtin is done by passing the portion K through filters and columns and allowing it to percolate through the solid material and the filtrate having Azadirachtin in varying concentration ranging up to 25% and above azadirachtin is collected. Azadirachtin concentrate L is the Azadirachtin extract obtained through mentioned different systems and process.

V. Preparing Extract of Custard Apple a. The immature fruits of Annona Squmosa and Annona Reticulata are collected and washed in water containing fungicides like Dinitro Dibromo propane 2,3 diol f and shade dried to remove the surface moisture, but not allowing the fruits to whither.

b. The seeds of custard apple (Annona Squmosa and Annona Reticulata) are collected by crushing matured fruits in water through wooden agitators without injuring the seeds. The pulp is separated from the seeds through water washing, filtration, methodologies and the seeds are collected and sun dried. After sun drying, the seeds are cleaned by winnowing. The seeds are dried. Natural leaves of custard apple are collected and sun dried and pulverized.

c. The immature fruits, the seeds and leaves are mixed and crushed. The crushing is done using power driven wooden crushers (rotary crushers) or grinding stone. The proportion is 1:1 of immature fruits and seeds by weight and the crushed leaf powder are added to desired level which is standardized by eyes which is done by experience.

d. Dough is obtained through crushing. The said dough is then soaked in water 20 Kgs of the dough in 20 Litres of water for 3 hours. The said dough is further ground in a grinder, if needed, up one or more polar solvents to make it to a semi solid portion.

e. The preparation of immature fruits, immature seeds and the leaves is in the ratio of 1:1:0.2. normally f. The dough is taken into a hot vapour percolator where they have porous bottom and ease out heat.

g. To separate the constituents from the dough one or more polar solvent vapours are passed through the dough which condenses and percolates and extracts the constituents. The vapour of polar solvent is almost 100%. For every 10 Kgs. of dough mix 30 litres of 99% polar solvent is used for vapour condensate.

h. The vapour condensate percolates and produces an infusion, which is collected.

i. The dough containing the polar solvent after the solvent extraction, the residue is further subjected to filtration for separating the solid and liquid, which is done in two methods.
   (a) In the first method, the residue dough mixture is subjected to centrifugation with a natural centrifuge at a speed of 6000 rpm for an hour and the solid and liquid phases are separated.
   (b) In the second method, the residue dough mixture is packed in filter bags and using and hydraulic press the liquid phase is squeezed out under high pressure. Normally, the pressure used in the hydraulic press is 100 to 110 psi. When using a hydraulic press, if by chance any solid particle contaminates the infusion that is a liquid phase, it is separated either through a process of filtration and sedimentation or through centrifugation.

j. The liquid phase obtained in either case is processed though different solvent extractions, if needed.

k. Further, the solvent extraction is put through vaccum vapouration process wherein more than 90% of the solvent and mixtures thereof is recovered. The slurry that is left over is called the extract of custard apple, which is used in the preparation of the combination pesticide, viz., neem oil custard apple preparation. (M)

VI. Emulsification of Neem Oil a. The prepared neem oil A is subjected to reduction in density through a thermic process in a specialized vessel and to dilution with mineral oils like Aromax (like Aromax and other mineral oil of petroleum origin), Ethoxylation of the vegetable oil.

b. Emulsification of the said oil A is done with ionic and non-ionic emulsifiers of vegetable origin, separately or in combination. The appropriate selection of emulsifier is done to arrive at a HLB value of the emulsifier ranges between 11 to 12. The emulsifier is added to the neutral oil proportionately and churned for 3 hours at 6000 rpm. The time for churning will be varied depending upon the emulsification and it may be less or more than 3 hours.

c. Addition of custard apple extract (M) during emulsification, means adding of ethoxylated vegetable oils containing fatty alcohols in desired proportion described herein earlier.

d. The UV stabilizer and the stabilization of either synthetic chemical or natural origin like Para Amino Benzoic Acid, palm sugar, and molasses. (Sterilized) are added proportionately and stirred in an emulsifier tank to achieve the emulsification oil (N).

VII. Dosing & Formulation of Final Concentrate

The dosing of the emulsified oil (N) with azadirachtin concentrate extract L until desired strengths of 300 ppm of azadirachtin is achieved in the emulsion concentrate.

I claim:

1. A process for making a neem oil-based emulsion concentrate containing at least 300 ppm of azadirachtin, comprising the steps of, in order:
   a) preparing neem seeds from neem fruits,
   b) preparing neem seed kernels from the neem seeds,
   c) preparing neem oil from the neem seeds,
   d) preparing an azadirachtin concentrate extract containing at least 300 ppm of azadirachtin by solvent extraction of the neem seed kernels and thereafter purifying by reverse osmosis,
   e) reducing an oil density of the neem oil by thermic processing under controlled conditions,
   f) emulsifying the neem oil,
   g) dosing the emulsified neem oil with the azadirachtin concentrate extract to yield a pesticide containing at least 300 ppm of azadirachtin.

2. The process of claim 1, wherein the process further comprises the step of:
   h) adding stabilizing agents and UV screens to the pesticide to yield the neem oil-based emulsion concentrate containing at least 300 ppm azadirachtin.

3. The process of claim 1, wherein step (a) comprises the steps of, in order:
   i) depulping of fruits to separate the seeds,
   ii) coating the seeds with antifungal and antibacterial material, and
   iii) drying the seeds in open air or at a controlled temperature to a predetermined moisture level.

4. The process of claim 1, wherein step c) comprises the steps of, in order:
   i) cold crushing of dry seeds in wooden crushers, and
   ii) adding palm sugar as a separating agent to separate the neem oil from a neem cake.

5. The process of claim 1, wherein step c) comprises the steps of, in order:
   i) neutralizing aflatoxin in the neem oil with chemicals,
   ii) separating fatty acids from the neem oil by employing a lye solution to precipitate the fatty acids,
   iii) separating and filtering the neem oil and the precipitated fatty acids,
   iv) separating a low density oil portion of the neem oil, and
   v) adding preservatives.

6. The process of claim 1, wherein step d) comprises the steps of, in order:
   i) crushing a neem cake to particle size of 60 mesh and then grinding obtained neem cake particles to a powder,
   ii) separately soaking the prepared seeds and the powder in water for 12 to 14 hours or until the seed kernels are softened,
   iii) grinding the soaked seeds and soaked powder to obtain a dough using a polar solvent,
   iv) passing polar solvent vapors through the dough to condense and to percolate soluble terpenoids to obtain a first condensate,
   v) vaporizing excess polar solvent from the first condensate,
   vi) condensing the first condensate by a cold vacuum evaporator process,
   vii) filtrating the first condensate at a temperature of 30–70° C.,
   viii) extracting a liquid portion containing azadirachtin and other triterpenoids from an organic potion of the first condensate using a non-polar solvent,
   ix) separating solid and liquid phases of the dough by mechanical means,
   x) concentrating the liquid phase of ix) which contains the terpenoids to a slurry,
   xi) extracting a second condensate from a solid biomass residue of the dough by using individual and/or a combination of solvents in an effective amount thereof,
   xii) concentrating the second condensate to obtain an extract with a concentration of terpenoids by solvent extraction, and wherein the extract further comprises a concentration of azadirachtin from 10 to 25%,
   xiii) collecting and mixing of the first and second condensates to yield a semi-pure slurry,
   xiv) filtering the semi-pure slurry by a reverse osmosis process to separate compounds with a molecular weight<1000 to obtain a filtered slurry containing azadirachtin, and
   xv) purifying the filtered slurry to obtain a filtrate having an azadirachtin content in the extract of at least 20%.

7. The process of claim 1, wherein step e) comprises the steps of, in order:
   i) reducing the oil density of the neem oil by a controlled thermic treatment of the oil wherein the thermic process is carried out in specially designed vessels,
   ii) diluting the neem oil by adding mineral diluents and/or other vegetable oils with lower densities than that of the neem oil,
   iii) adding emulsifiers under constant stirring and agitation for 3 hours at 6000 rpm,
   iv) adding an extract from custard apple which is obtained by extracting a crushed biomass of immature custard apple fruits, seeds and matured leaves.

8. The process of claim 1, wherein step f) comprises stirring neem oil by agitation and dosing thereof with the azadirachtin extract until the neem oil contains a concentrations of at least 300 ppm azadirachtin.

9. The process of claim 1, wherein step g) comprises, in order:
   i) adding stabilizing agents from natural and/or synthetic sources either alone or in combination to the emulsified neem oil, and
   ii) adding UV screening agents to the emulsified neem oil to obtain the neem oil based emulsion concentrate.

10. The process of claim 2, wherein the antifungal material used in coating neem seeds is chosen from the group consisting of *Trichoderma Viride, Trichoderma Hamatum, Trichoderma Harzianum* and mixtures thereof.

11. The process of claim 10, wherein the antifungal material used for coating neem seeds is in a ratio of 1:1:1 consisting of *Trichoderma Viride; Trichoderma Hamatum; Trichoderma Harzianum*.

12. The process of claim 5, wherein the chemicals used in the neutralization process are chosen from the group consisting of sodium chloride, calcium chloride, silica dioxide, aluminum hydroxide and mixtures thereof.

13. The process of claim 12, wherein at least one of the chemicals are in a mixture comprising 98% sodium chloride, 98% calcium chloride, 90% silica dioxide, and 95% aluminum hydroxide.

14. The process of claim 5, wherein the lye solution is a caustic soda solution.

15. The process of claim 5, wherein the lye solution is a 48% caustic soda solution and a quantum of NaOH or the lye solution is added in an effective amount thereof.

16. The process of claim 6, wherein the polar solvent is chosen from the group consisting of methanol, ethanol, methyl ethyl ketone, methyl-tertiary-butyl-ether and mixtures thereof, wherein the polar solvent is employed for grinding in preparing the dough.

17. The process of claim 6, wherein the polar solvent vapours are chosen from the group consisting of methanol, ethanol, methyl ethyl ketone, methyl-tertiary-butyl-ether, and mixture thereof, wherein the polar solvent vapours are employed in the percolation process.

18. The process of claim 6, wherein the polar solvent vapours are in a ratio of 1:1:1:1 consisting of methanol:ethanol:methyl ethyl ketone:methyl-tertiary-butyl-ether are in a ratio 1:1:1:1 when used in the percolation process.

19. The process of claim 6, wherein the non-polar solvent is chosen from the group consisting of hexane, petroleum ether, dichloro methane and mixtures thereof.

20. The process of claim 6, wherein the mechanical means comprise centrifuging or separating by a hydraulic squeezing process the residual dough mixture into the liquid and the solid phases.

21. The process of claim 20, wherein the residual dough mixture is centrifuged at 6000 rpm for at least one hour.

22. The process of claim 20, wherein the hydraulic squeezing process comprises applying a pressure of 100–110 psi to separate the liquid portion from the remaining neem seed kernel biomass which contains both liquid and solid portions.

23. The process of claim 13, wherein the neutralization process employs 1% sodium chloride, 2% calcium chloride, 66% silica dioxide and 12% aluminum hydroxide.

24. The process of claim 15, wherein the lye solution comprises 30 litres of 40% NaOH solution for 1000 litres of neem oil having 10% of free fatty acid.

\* \* \* \* \*